United States Patent
Griffith et al.

(10) Patent No.: US 9,602,669 B1
(45) Date of Patent: *Mar. 21, 2017

(54) CALL CENTER ANXIETY FEEDBACK PROCESSOR (CAFP) FOR BIOMARKER BASED CASE ASSIGNMENT

(71) Applicant: International Business Machines Corporation, Armonk, NY (US)

(72) Inventors: Douglas J. Griffith, Spicewood, TX (US); Anil Kalavakolanu, Austin, TX (US); Srinivasa R. Muppala, Austin, TX (US); Srinivasa M. Raghavan, Round Rock, TX (US); Yanhua Yang, Cedar Park, TX (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/197,637

(22) Filed: Jun. 29, 2016

Related U.S. Application Data

(63) Continuation of application No. 14/983,381, filed on Dec. 29, 2015, now Pat. No. 9,426,292.

(51) Int. Cl.
*H04M 3/00* (2006.01)
*H04M 5/00* (2006.01)
(Continued)

(52) U.S. Cl.
CPC .... *H04M 3/5232* (2013.01); *G06Q 10/06311* (2013.01)

(58) Field of Classification Search
CPC .................................................. H04M 3/5175
(Continued)

(56) References Cited

U.S. PATENT DOCUMENTS

| 5,447,524 A | * | 9/1995 | Alt ..................... A61N 1/36542 |
| | | | 607/19 |
| 6,605,038 B1 | | 8/2003 | Teller et al. |

(Continued)

OTHER PUBLICATIONS

List of IBM Patents or Patent Applications Treated as Related Form.
(Continued)

*Primary Examiner* — William Deane, Jr.
(74) *Attorney, Agent, or Firm* — Sherman IP LLP; Kenneth L. Sherman; Hemavathy Perumal

(57) ABSTRACT

One embodiment provides a method for allocating assignments based on workload and physiological stress. The method comprises maintaining a queue of logged-in service representatives, and, in response to receiving a service request for a new assignment, scanning the queue to determine a subset of potential service representatives to assign the new assignment to. A corresponding workload level of each service representative of the subset is the smallest among all service representatives of the queue. For each service representative of the subset, a corresponding anxiety level is determined based on physiological sensor data captured by a wearable tracking device attached to the service representative. The new assignment is assigned to a service representative of the subset, the service representative having a corresponding anxiety level that is the smallest among all service representatives of the subset.

1 Claim, 6 Drawing Sheets

(51) Int. Cl.
*H04M 3/523* (2006.01)
*G06Q 10/06* (2012.01)

(58) Field of Classification Search
USPC ....... 379/265.01–265.14, 266.01–266.1, 309
See application file for complete search history.

(56) References Cited

U.S. PATENT DOCUMENTS

| | | |
|---|---|---|
| 7,027,621 B1 | 4/2006 | Prokoski |
| 7,100,818 B2 | 9/2006 | Swaine |
| 7,151,826 B2 | 12/2006 | Shambaugh et al. |
| 8,140,368 B2 | 3/2012 | Eggenberger et al. |
| 8,164,461 B2 | 4/2012 | Bischoff |
| 8,494,507 B1 | 7/2013 | Tedesco et al. |
| 8,498,403 B1 | 7/2013 | Coughlan et al. |
| 8,533,005 B2 | 9/2013 | Eggenberger-Wang et al. |
| 9,195,900 B2 | 11/2015 | Gu et al. |
| 2004/0062363 A1 | 4/2004 | Shambaugh et al. |
| 2005/0069852 A1 | 3/2005 | Janakiraman et al. |
| 2005/0163302 A1 | 7/2005 | Mock et al. |
| 2006/0293921 A1 | 12/2006 | McCarthy et al. |
| 2008/0165017 A1 | 7/2008 | Schwartz |
| 2010/0324427 A1 | 12/2010 | Devot et al. |
| 2011/0040191 A1 | 2/2011 | Kyle et al. |
| 2011/0125063 A1 | 5/2011 | Shalon et al. |
| 2013/0051545 A1* | 2/2013 | Ross ............... H04M 3/523 379/265.02 |
| 2013/0142322 A1 | 6/2013 | Grasso |
| 2013/0231574 A1 | 9/2013 | Tran |
| 2013/0345568 A1 | 12/2013 | Mestha et al. |
| 2014/0051940 A1 | 2/2014 | Messerschmidt |
| 2014/0072136 A1* | 3/2014 | Tenenbaum ........... G08B 21/06 381/74 |
| 2014/0221781 A1 | 8/2014 | Schrauf et al. |
| 2015/0141789 A1 | 5/2015 | Knight et al. |

OTHER PUBLICATIONS

Anonymous, "Driven from distraction", The Economist, Apr. 25, 2015, pp. 1-6, The Economist Newspaper Limited, United States, [downloaded from http://www.economist.com/news/science-and-technology/21648999-how-save-phone-using-motorists-themselves-driven-distraction].

* cited by examiner

CALL CENTER ANXIETY FEEDBACK PROCESSOR (CAFP) FOR BIOMARKER BASED CASE ASSIGNMENT

The present invention generally relates to workload management, and more particularly, automatic case assignment based in part on biomarkers.

BACKGROUND

Service automation invariably depends on rigorous allocation strategies and tools to handle customer cases efficiently. In the present context of case management or incident management, a business of services may utilize an automatic allocation tool to assign cases to service personnel. Several existing automatic allocation tools implement a fair-share workload policy based on workload alone. Assigning cases based on workload alone, however, may diminish effectiveness of skilled service personnel available to handle new cases.

SUMMARY

One embodiment provides a method for allocating assignments based on workload and physiological stress. The method comprises, in response to a log-in by a service representative, adjusting a corresponding status indicator for the service representative from an unavailable status indicating the service representative is unavailable to an available status indicating the service representative is available. The method further comprises maintaining a queue of logged-in service representatives. Each service representative of the queue has a corresponding workload level indicating amount of assignments assigned to the service representative. In response to receiving a service request for a new assignment, the queue is scanned to determine a subset of potential service representatives to assign the new assignment to. A corresponding status indicator of each service representative of the subset is set to the available status, and a corresponding workload level of the service representative is the least among all service representatives of the queue. For each service representative of the subset, a corresponding anxiety level representing a degree of physiological stress of the service representative is determined based on physiological sensor data captured by a wearable tracking device attached to the service representative. The new assignment is assigned to a service representative of the subset, where a corresponding anxiety level of the service representative is the least among all service representatives of the subset. The method further comprises monitoring at least one anxiety level corresponding to at least one service representative of the queue. At least one assignment is selectively re-assigned based in part on the at least one anxiety level monitored. In response to a corresponding anxiety level of an available service representative of the queue exceeding a configurable threshold indicating increased physiological stress, a corresponding status indicator for the service representative is adjusted from the available status to the unavailable status.

These and other aspects, features and advantages of the invention will be understood with reference to the drawing figures, and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

Figure 1:
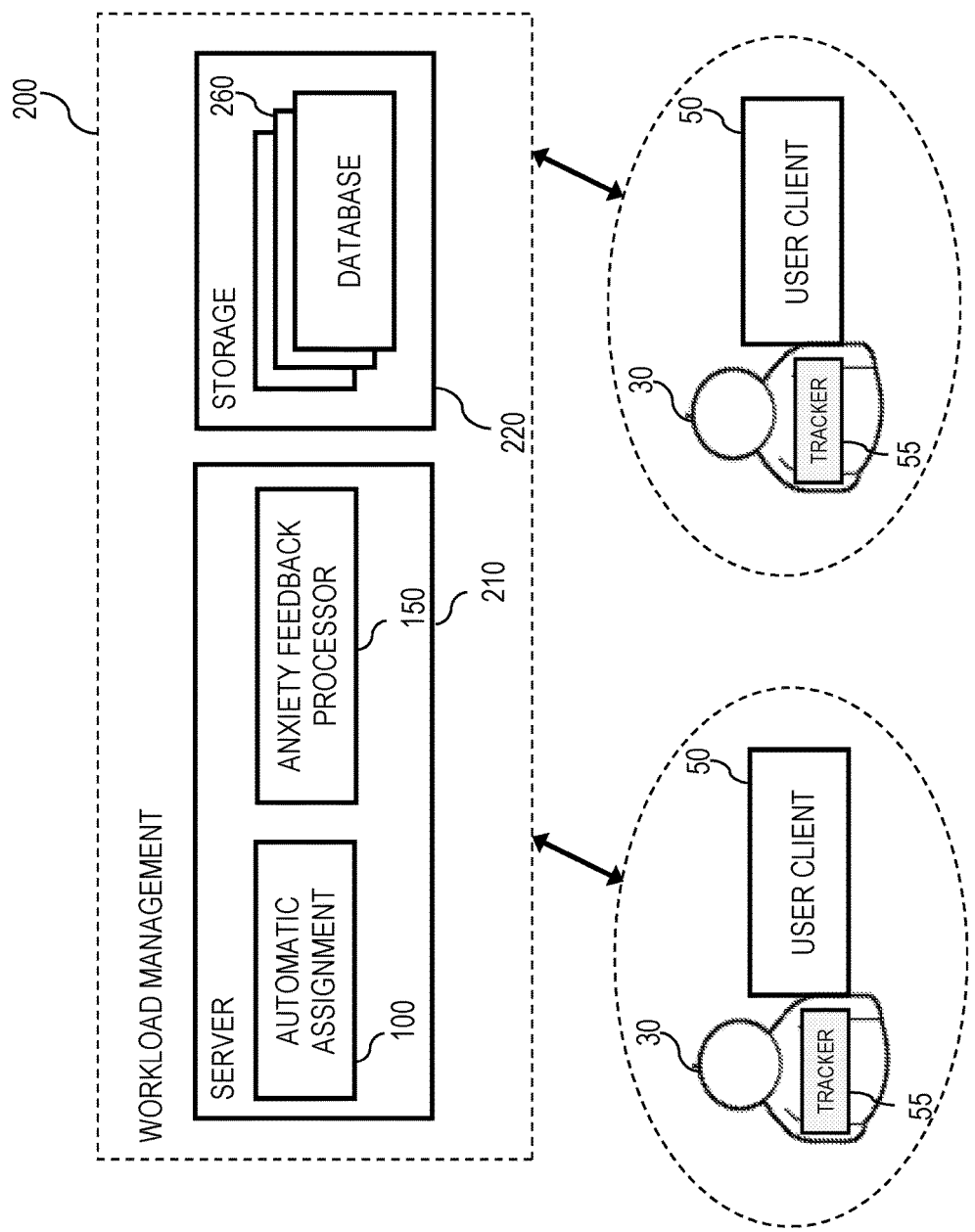
FIG. 1 illustrates an example workload management system, in accordance with an embodiment of the invention.

The detailed description explains the preferred embodiments of the invention, together with advantages and features, by way of example with reference to the drawings.

DETAILED DESCRIPTION

The present invention generally relates to workload management, and more particularly, automatic case assignment based in part on. One embodiment provides a method for allocating assignments based on workload and physiological stress. The method comprises, in response to a log-in by a service representative, adjusting a corresponding status indicator for the service representative from an unavailable status indicating the service representative is unavailable to an available status indicating the service representative is available. The method further comprises maintaining a queue of logged-in service representatives. Each service representative of the queue has a corresponding workload level indicating amount of assignments assigned to the service representative. In response to receiving a service request for a new assignment, the queue is scanned to determine a subset of potential service representatives to assign the new assignment to. A corresponding status indicator of each service representative of the subset is set to the available status, and a corresponding workload level of the service representative is the least among all service representatives of the queue. For each service representative of the subset, a corresponding anxiety level representing a degree of physiological stress of the service representative is determined based on physiological sensor data captured by a wearable tracking device attached to the service representative. The new assignment is assigned to a service representative of the subset, where a corresponding anxiety level of the service representative is the least among all service representatives of the subset. The method further comprises monitoring at least one anxiety level corresponding to at least one service representative of the queue. At least one assignment is selectively re-assigned based in part on the at least one anxiety level monitored. In response to a corresponding anxiety level of an available service representative of the queue exceeding a configurable threshold indicating increased physiological stress, a corresponding status indicator for the service representative is adjusted from the available status to the unavailable status.

Several existing automatic allocation tools implement a fair-share workload policy based on workload alone. In spite of varying workloads, anxiety levels of service personnel depend more on psychological factors than on workload alone. Embodiments of the invention provide an automatic allocation tool that factors into account biomarkers such as physiological stress, thereby improving business outcomes and client satisfaction. One embodiment factors into account emotional content of service representatives (e.g., case recipients at a call center) during fair-share auto-assignment using non-invasive, wearable activity trackers. The trackers capture biomarkers, such as Heart Rate Variability (HRV), GSR (Galvanic Skin response) and temperature, for use in determining and categorizing physiological stress and anxiety of the service representatives. One embodiment combines a fair-share workload policy and biomarkers data to provide a case assignment tool with improved accuracy.

In this specification, let the term "anxiety level" denote a degree of physiological stress and anxiety experienced by an individual (e.g., a service representative) during a particular duration of time (e.g., during a work shift of a service representative). Let the term "case" generally denote a customer case or a customer service call that requires handling by a service representative. Let the term "workload level" denote an amount of workload (e.g., number of cases) assigned to an individual (e.g., a service representative) during a particular duration of time (e.g., during a work shift of a service representative).

FIG. 1 illustrates an example workload management system 200, in accordance with an embodiment of the invention. The system 200 comprises one or more server devices 210, and one or more storage devices 220. The storage devices 220 maintain one or more databases 260. One or more application units may execute/operate on the server devices 210, such as an anxiety feedback processor unit 150 and an automatic assignment unit 100.

As described in detail later herein, the anxiety feedback processor unit 150 is configured to: (1) monitor real-time anxiety levels of a set of service representatives 30, (2) identify a service representative 30 of the set having the smallest anxiety level (i.e., the service representative 30 of the set with the least amount of physiological stress and anxiety), and (3) provide feedback to the automatic assignment unit 100, the feedback relating to at least one anxiety level of at least one service representative 30 of the set.

As described in detail later herein, the automatic assignment unit 100 is configured to allocate new assignments (e.g., new cases or new calls) to one or more service representatives 30 of the set based on availability of each service representative 30, workload level of each service representative 30, and feedback from the anxiety feedback processor unit 150. The automatic assignment unit 100 implements an improved/enhanced fair-share workload policy that considers factors other than workload, such as physiological stress and anxiety. The ability to account for dynamic nature of human emotions in workload management may also help reduce or minimize occurrence of stress-induced work-related incidents.

A service representative 30 (e.g., a customer service representative working at a call center) may access and log into the system 200 using an electronic device ("user client") 50, such as a desktop computer, a laptop computer, a tablet, a mobile phone, etc. In one embodiment, each device 50 exchanges data with the system 200 over a connection (e.g., a wireless connection, a wired connection, or a combination of the two). Each service representative 30 has a corresponding wearable tracking device ("tracker") 55 worn by the service representative 30 (e.g., the tracker 55 attached to a piece of clothing or body part of the service representative 30). As described in detail later herein, a tracker 55 worn by a service representative 30 is configured to capture physiological sensor data associated with the service representative 30; the physiological sensor data captured is provided to the anxiety feedback processor unit 150 for determining an anxiety level of the service representative 30. Examples of physiological sensor data captured by a tracker 55 include biomarkers such as HRV, GSR, temperature, etc.

Figure 2:
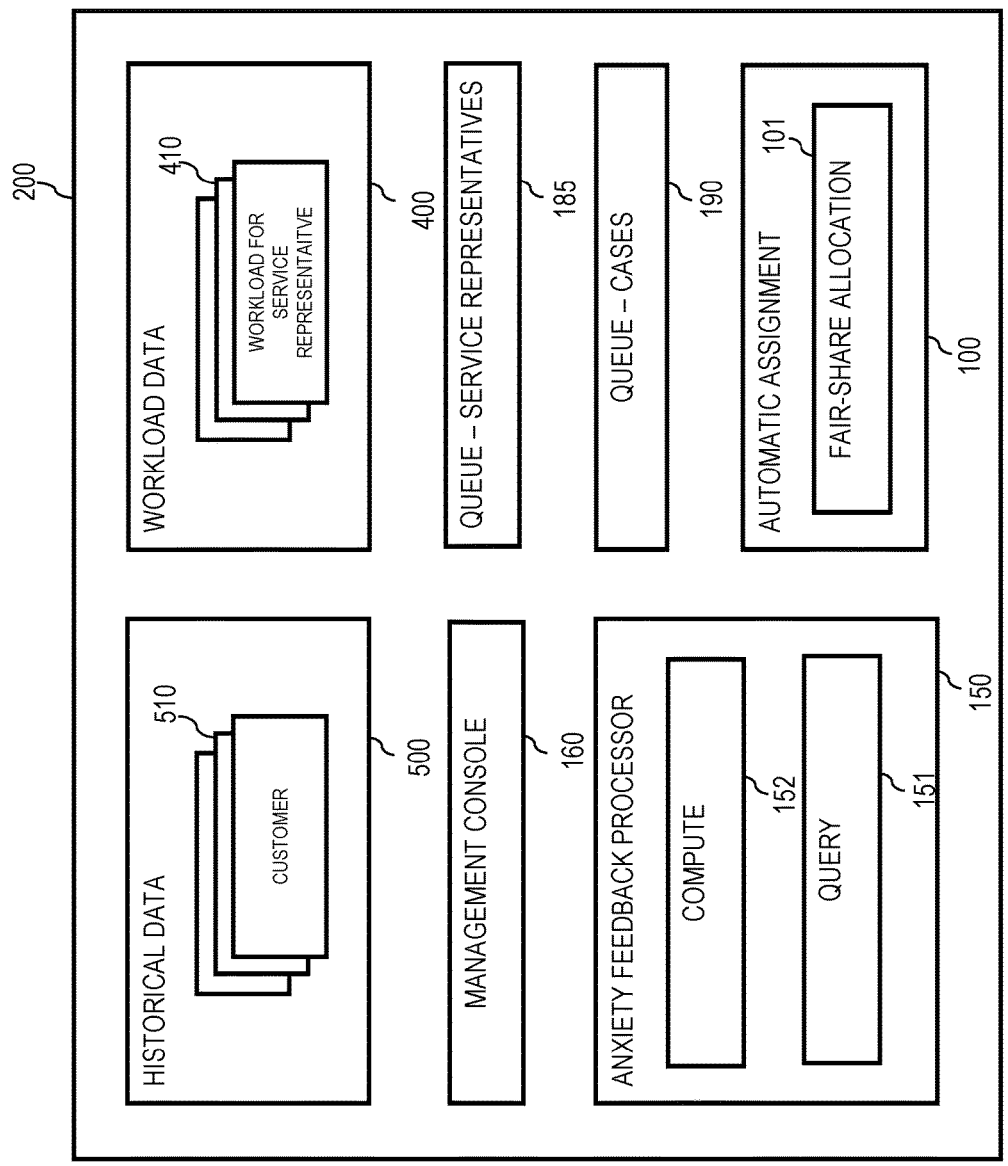
FIG. 2 illustrates the workload management system in detail, in accordance with an embodiment of the invention.

FIG. 2 illustrates the example workload management system 200 in detail, in accordance with an embodiment of the invention. The system 200 comprises a management console unit 160 configured to receive, as input, each of the following: (1) one or more service requests from one or more customers/clients, (2) physiological sensor data from one or more trackers 55, (3) one or more log-in and/or log-out requests from one or more service representatives 30, (4) one or more re-sync requests, and (5) one or more configurable thresholds. Each service request comprises a request for a service representative 30 to service/handle a new case assignment. A re-sync request comprises a request to query/re-query a tracker 50 for physiological sensor data captured by the tracker 50.

The system 200 maintains a collection 400 of workload data sets 410. Each workload data set 410 corresponds to a service representative 30, and comprises a list of cases assigned to the service representative 30 (e.g., cases or calls assigned to the service representative 30 for handling). In one embodiment, the collection 400 may be maintained on at least one database 260 (FIG. 1) of the storage devices 220 (FIG. 1).

Each service representative 30 has a corresponding identifier, and a corresponding status indicator indicating availability of the service representative 30. In one embodiment, a status indicator for a service representative 30 may be set to one of the following statuses: (1) an "unavailable" status indicating the service representative 30 is unavailable for a new case assignment, or (2) an "available status" indicating the service representative 30 is available for a new case assignment. A service representative 30 is unavailable for a new case assignment if the service representative 30 has not logged-in to the system 200, the service representative 30 is busy with his/her current workload, or an anxiety level of the service representative 30 is high (e.g., exceeds a configurable threshold). A service representative 30 is available for a new case assignment if the service representative 30 has logged-in to the system 200 and is free to service/handle a new case assignment.

In one embodiment, the system 200 may use visual indicators to highlight a current status of a service representative 30. For example, if a status indicator for a service representative 30 is set to the "unavailable" status, a corresponding status light for the service representative 30 may be red to indicate that the service representative 30 is unavailable. If a status indicator for a service representative 30 is set to the "available" status, a corresponding status light for the service representative 30 may be green to indicate that the service representative 30 is available.

The system 200 further maintains a first queue 185 of service representatives 30 who have logged into the system 200. In response to a receiving a log-in request from a service representative 30 via a device 50, the system 200 logs in the service representative 30, adds the service representative 30 to the first queue 185 (i.e., the system 200 adds a corresponding identifier for the service representative 30 to the first queue 185), and adjusts a corresponding identifier for the service representative 30 from the "unavailable" status to the "available" status. In response to a receiving a log-out request from a service representative 30 via a device 50, the system 200 adjusts a corresponding identifier for the service representative 30 from the "available" status to the "unavailable" status, removes the service representative 30 from the first queue 185 (i.e., the system 200 removes a corresponding identifier for the service representative 30 from the first queue 185), and logs out the service representative 30.

The system 200 further maintains a second queue 190 of cases. In response to a receiving a service request from a customer/client, the system 200 adds a new case associated with the service request to the second queue 190. A case is removed from the second queue 190 when a service representative 30 assigned the case has finished servicing/handling the case (e.g., if the case is a customer service call, the call has ended).

The anxiety feedback processor unit 150 comprises a query module 151 and a compute module 152. The query module 151 is configured to query/re-query a tracker 50 carried by a service representative 30 for physiological sensor data captured by the tracker 50 when either the service representative 30 logs in to the system 200 or a re-sync request is received. The compute module 152 is configured to compute an anxiety level of a service representative 30 based on physiological sensor data captured by a tracker 50 worn by the service representative 30.

The automatic assignment unit 100 comprises a fair-share allocation module 101 that combines a fair-share workload policy with biomarkers data. In response to receiving a service request from a customer/client, the fair-share allocation module 101 is configured to: (1) scan the first queue 185 for available service representatives 30, (2) for each available service representative 30 in the first queue 185, determine a corresponding workload level of the service representative 30 based on a corresponding workload data record 410 for the service representative 30, (3) select, from the first queue 185, at least one available service representative 30 having the smallest workload level among all the available service representatives 30 in the first queue 185, and (4) trigger the anxiety feedback processor unit 150 to determine, for each selected service representative 30, a corresponding anxiety level.

For each selected service representative 30, the query unit 151 of the anxiety feedback processor unit 150 is configured to query a corresponding tracker 55 worn by the service representative 30 for physiological sensor data captured by the tracker 55. For each selected service representative 30, the compute unit 152 of the anxiety feedback processor unit 150 is configured to compute a corresponding anxiety level based on physiological sensor data captured by a tracker 50 worn by the service representative 30. The compute unit 152 further determines which of the selected service representatives 30 has a corresponding anxiety level that is the smallest among all selected service representatives 30.

In one embodiment, the fair-share allocation module 101 assigns a new case to a service representative 30 in the first queue 185 having the smallest workload level and the smallest anxiety level among all available service representatives 30 in the first queue 185.

In one embodiment, if each available service representative 30 in the first queue 185 has the same workload level, the fair-share allocation module 101 assigns a new case to a service representative 30 in the first queue 185 having the smallest anxiety level among all available service representatives 30 in the first queue 185.

In one embodiment, the fair-share allocation module 101 selects, from the first queue 185, a subset of at least two available service representatives 30 having the smallest workload level among all available service representatives 30 in the first queue 185, and assigns a new case to a service representative 30 of the subset having the smallest anxiety level among all service representatives 30 of the subset.

In one embodiment, the compute module 152 is configured to monitor an anxiety level of a service representative 30 while the service representative 30 is working on an assigned case. For example, the compute module 152 may compute mean, mode and average anxiety levels of a service representative 30 while the service representative 30 is working on an assigned case; the anxiety levels computed are maintained for the duration the service representative 30 is working on the assigned case (e.g., duration of a customer service call or number of hours spent working on a customer case).

In one embodiment, if an anxiety level of an available service representative 30 in the first queue 185 exceeds a configurable threshold indicating elevated/increased physiological stress and anxiety, the anxiety feedback processor unit 150 is configured to change a corresponding status identifier for the service representative 30 from the "available" status to the "unavailable" status. In one embodiment, each service representative 30 has a corresponding configurable threshold (i.e., different thresholds for different service representatives 30).

In one embodiment, if an average anxiety level for at least one service representative 30 in the first queue 185 exceeds a configurable threshold indicating elevated/increased physiological stress and anxiety, the anxiety feedback processor unit 150 is configured to trigger the automatic assignment unit 100 to re-assign one or more cases in the second queue 190.

In one embodiment, the system 200 maintains historical data on customers/clients. For example, the system 200 maintains a collection 500 of customer data sets 510. Each customer data set 510 corresponds to a customer/client, and comprises information indicating degree of difficulty in dealing with the customer/client based on prior experiences. The automatic assignment unit 100 may utilize the historical data on customers to minimize assignment of cases for difficult customers to newer service representatives 30.

For example, the system 200 may record anxiety levels of a service representative 30 handling a customer service call from a customer/client, and maintain the recorded anxiety levels in a customer data record 510 corresponding to the customer/client. When the system 200 receives another customer service call from the same customer/client, the system 200 predicts an expected anxiety level based on one or more prior experiences recorded in the customer data record 510, and assigns the call to an available service representative 30 based in part the expected anxiety level.

Figure 3A:
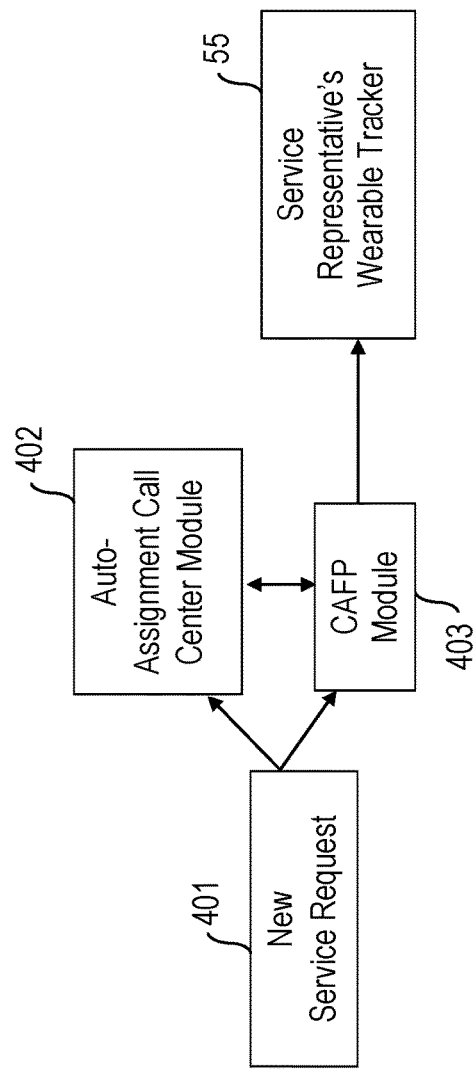
FIG. 3A is a block diagram of an example workload management system for a call center, wherein the workload management system implements a fair-share workload policy that considers factors other than workload, such as physiological stress and anxiety, in accordance with an embodiment of the invention.
Figure 3B:
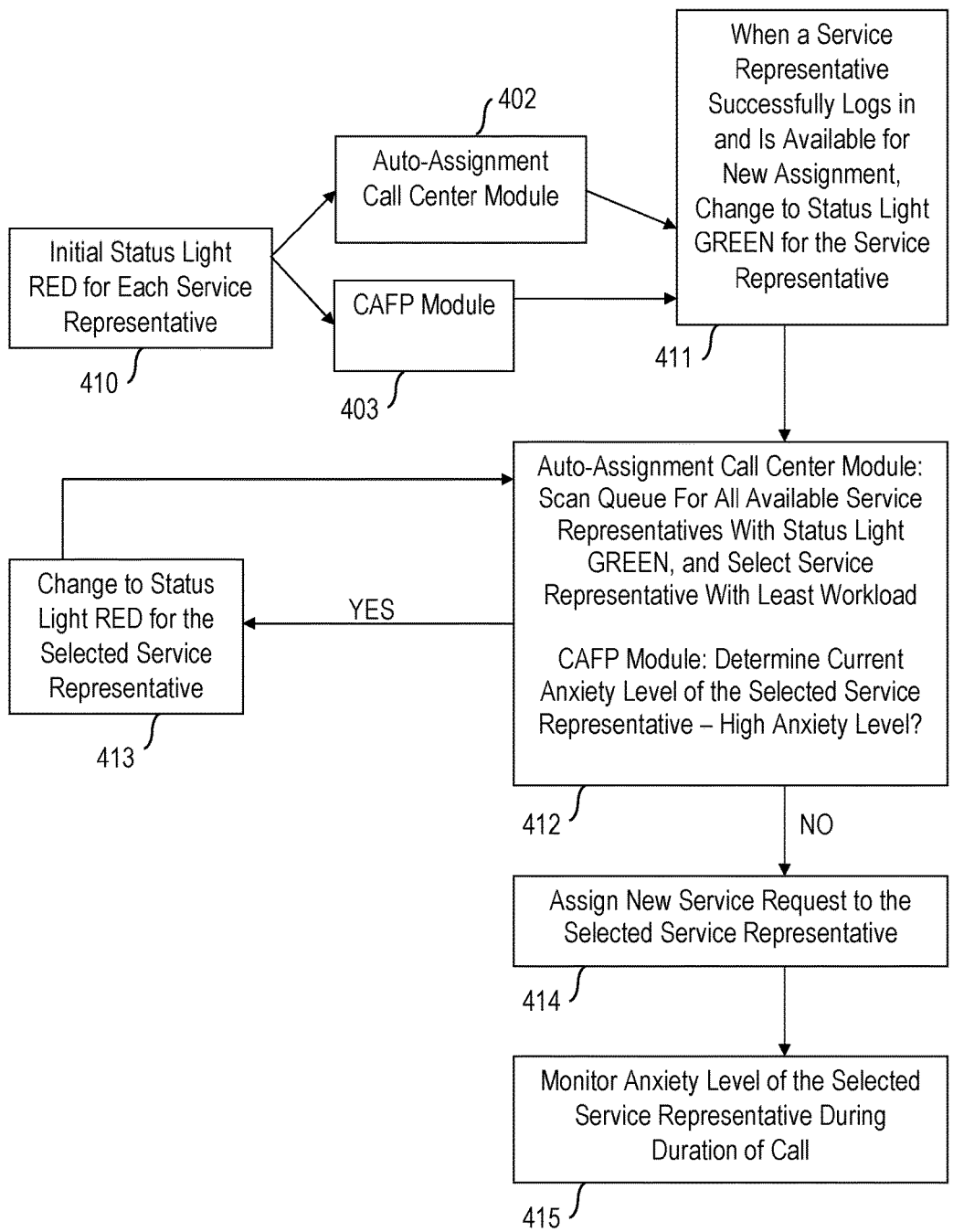
FIG. 3B is a flowchart of an example process for allocating new assignments using the workload management system in FIG. 3A, in accordance with an embodiment of the invention.
Figure 3C:
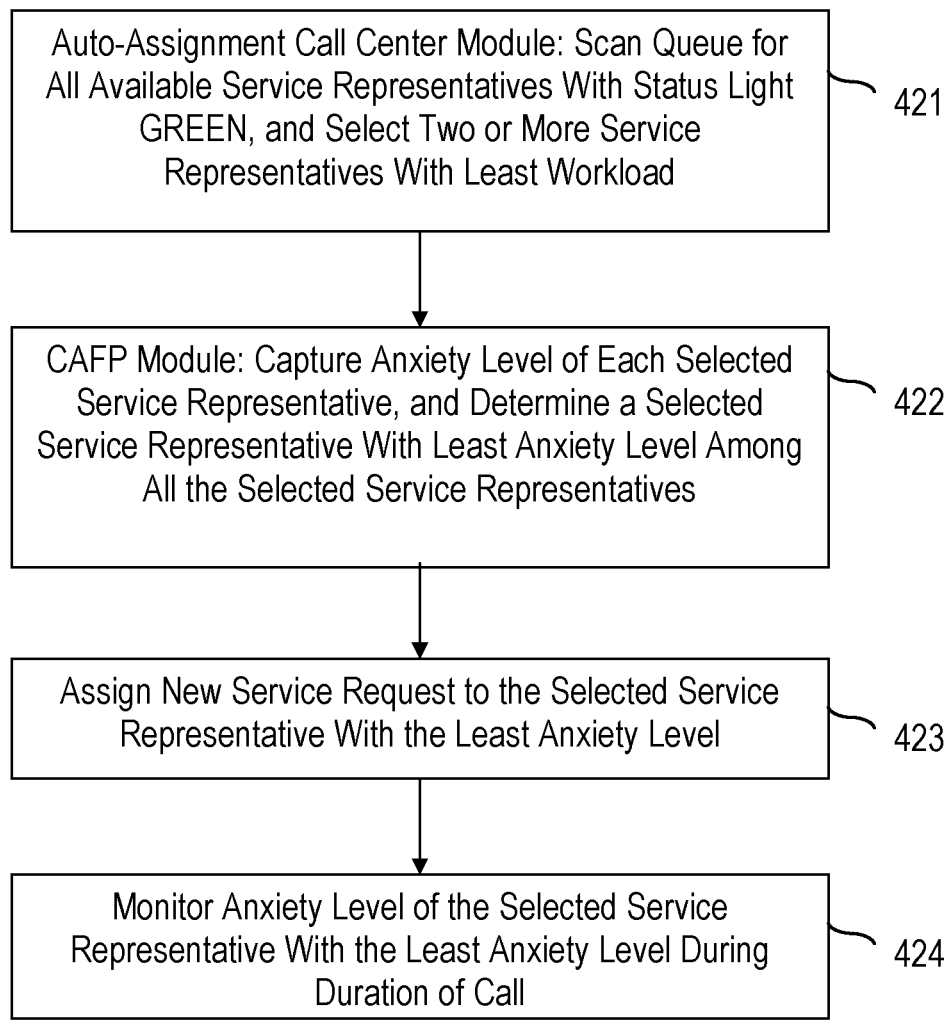
FIG. 3C is a flowchart of another example process for allocating new assignments using the workload management system in FIG. 3A, in accordance with an embodiment of the invention.

FIGS. 3A-3C illustrate an example implementation of a workload management system for a call center. FIG. 3A is a block diagram of an example workload management system 400 for a call center, wherein the workload management system 400 implements a fair-share workload policy that considers factors other than workload, such as physiological stress and anxiety, in accordance with an embodiment of the invention. The workload management system 400 comprises an automatic assignment call center module 402 and a call center anxiety feedback processor (CAFP) module 403. The automatic assignment call center module 402 is an example implementation of the automatic assignment unit 100, and is configured to perform operations described above for the automatic assignment unit 100. The CAFP module 403 is an example implementation of the anxiety feedback processor unit 150, and is configured to perform operations described above for the anxiety feedback processor unit 150.

The automatic assignment call center module 402 and the CAFP module 403 exchange data between one another (e.g., the automatic assignment call center module 402 exchanges information identifying one or more service representatives with least workload, and the CAFP module 403 exchanges information identifying one or more service representatives 30 with least anxiety level).

The workload management system 400 receives a new service request 401 (i.e., a request to handle a new incoming call at the call center from a customer/client), and forwards the new service request 401 to the automatic assignment call center module 402 and the CAFP module 403. The workload management system 400 utilizes the automatic assignment call center module 402 and the CAFP module 403 to determine a service representative to assign the new service request 401 to. The CAFP module 403 queries one or more trackers 50 worn by one or more service representatives for physiological sensor data.

FIG. 3B is a flowchart of an example process 410 for allocating new assignments using the workload management system 400 in FIG. 3A, in accordance with an embodiment of the invention. In process block 410, initial status light is red (i.e., unavailable) for each service representative. The automatic assignment call center module 402 and the CAFP module 403 are notified when a service representative logs in or logs out of the workload management system 400. In process block 411, when a service representative successfully logs in and is available for new assignment, change status light to green (i.e., available) for the service representative.

In process block 412, the automatic assignment call center module 402 scans queue for all available service representatives with status light set to green, and selects a service representative with least workload; the CAFP module 403 determines current anxiety level of the selected service representative, and whether the current anxiety level is high. If the current anxiety level is high, proceed to process block 413 where the status light for the selected service representative is changed to red (i.e., unavailable), and return to process block 412.

If the current anxiety level is not high, proceed to process block 414 where the new service request 401 is assigned to the selected service representative. In process block 415, anxiety level of the selected service representative is monitored during duration of call handled by the selected service representative.

FIG. 3C is a flowchart of another example process 420 for allocating new assignments using the workload management system 400 in FIG. 3A, in accordance with an embodiment of the invention. In process block 421, the automatic assignment call center module 402 scans queue for all available service representatives with status light set to green, and selects two or more service representatives with least workload. In process block 422, the CAFP module 403 captures anxiety level of each selected service representative, and determines a selected service representative with least anxiety level among all the selected service representatives. In process block 423, the new service request 401 is assigned to the selected service representative with the least anxiety level. In process block 424, anxiety level of the selected service representative with the least anxiety level is monitored during duration of call handled by the selected service representative.

Figure 4:
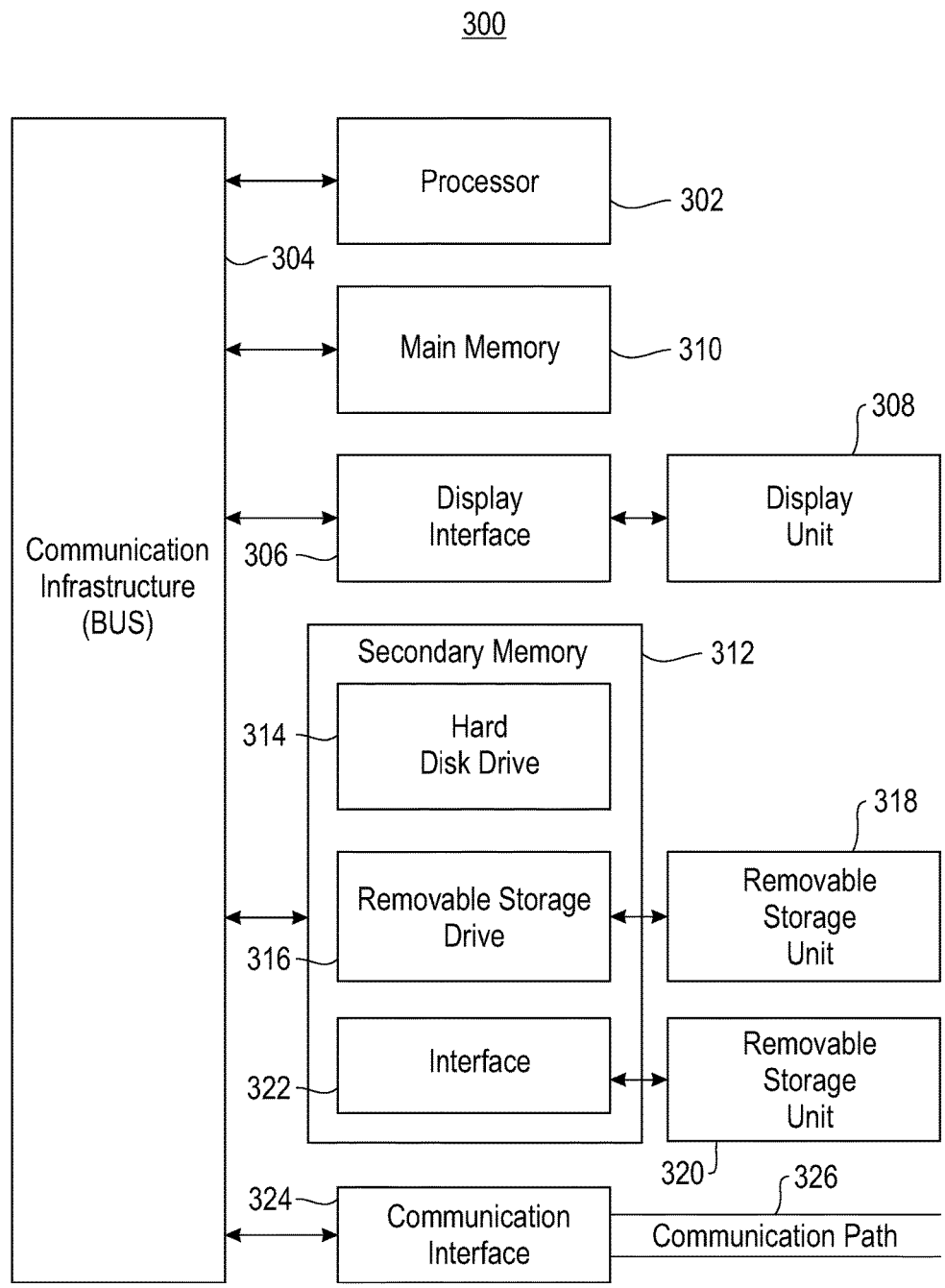
FIG. 4 is a high level block diagram showing an information processing system useful for implementing an embodiment of the present invention.

FIG. 4 is a high level block diagram showing an information processing system 300 useful for implementing one embodiment of the invention. The computer system includes one or more processors, such as processor 302. The processor 302 is connected to a communication infrastructure 304 (e.g., a communications bus, cross-over bar, or network).

The computer system can include a display interface 306 that forwards graphics, text, and other data from the communication infrastructure 304 (or from a frame buffer not shown) for display on a display unit 308. The computer system also includes a main memory 310, preferably random access memory (RAM), and may also include a secondary memory 312. The secondary memory 312 may include, for example, a hard disk drive 314 and/or a removable storage drive 316, representing, for example, a floppy disk drive, a magnetic tape drive, or an optical disk drive. The removable storage drive 316 reads from and/or writes to a removable storage unit 318 in a manner well known to those having ordinary skill in the art. Removable storage unit 318 represents, for example, a floppy disk, a compact disc, a magnetic tape, or an optical disk, etc. which is read by and written to by removable storage drive 316. As will be appreciated, the removable storage unit 318 includes a computer readable medium having stored therein computer software and/or data.

In alternative embodiments, the secondary memory 312 may include other similar means for allowing computer programs or other instructions to be loaded into the computer system. Such means may include, for example, a removable storage unit 320 and an interface 322. Examples of such means may include a program package and package interface (such as that found in video game devices), a removable memory chip (such as an EPROM, or PROM) and associated socket, and other removable storage units 320 and interfaces 322, which allows software and data to be transferred from the removable storage unit 320 to the computer system.

The computer system may also include a communication interface 324. Communication interface 324 allows software and data to be transferred between the computer system and external devices. Examples of communication interface 324 may include a modem, a network interface (such as an Ethernet card), a communication port, or a PCMCIA slot and card, etc. Software and data transferred via communication interface 324 are in the form of signals which may be, for example, electronic, electromagnetic, optical, or other signals capable of being received by communication interface 324. These signals are provided to communication interface 324 via a communication path (i.e., channel) 326. This communication path 326 carries signals and may be implemented using wire or cable, fiber optics, a phone line, a cellular phone link, an RF link, and/or other communication channels.

The present invention may be a system, a method, and/or a computer program product. The computer program product may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

From the above description, it can be seen that the present invention provides a system, computer program product, and method for implementing the embodiments of the invention. The present invention further provides a non-transitory computer-useable storage medium for implementing the embodiments of the invention. The non-transitory computer-useable storage medium has a computer-readable program, wherein the program upon being processed on a computer causes the computer to implement the steps of the present invention according to the embodiments described herein.

References in the claims to an element in the singular is not intended to mean "one and only" unless explicitly so stated, but rather "one or more." All structural and functional equivalents to the elements of the above-described exemplary embodiment that are currently known or later come to be known to those of ordinary skill in the art are intended to be encompassed by the present claims. No claim element herein is to be construed under the provisions of 35 U.S.C. section 112, sixth paragraph, unless the element is expressly recited using the phrase "means for" or "step for."

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A computer program product comprising a computer-readable hardware storage medium having program code embodied therewith, the program code being executable by a computer to implement a method for allocating assignments based on biomarkers, the method comprising:
    maintaining historical data indicating mean and mode anxiety levels corresponding to at least one service representative during at least one prior experience in which the at least one service representative serviced at least one prior assignment received at a service center;
    maintaining a first queue of logged-in service representatives, wherein each service representative of the first queue has a corresponding workload level indicating amount of assignments assigned to the service representative for servicing, and each service representative of the first queue is either available or unavailable for servicing an assignment;
    maintaining a second queue of assignments pending at the service center;
    in response to receiving a service request for a new assignment at the service center, adding the new assignment to the second queue, and scanning the first queue to determine a subset of potential service representatives to assign the new assignment to, wherein each service representative of the subset is available for servicing an assignment, and a corresponding workload level of each service representative of the subset is the least among all service representatives of the first queue;
    for each service representative of the subset, determining a corresponding anxiety level representing a degree of physiological stress of the service representative based on the historical data and biomarkers captured by a tracking device attached to the service representative, wherein the biomarkers include heart rate variability of the service representative, galvanic skin response of the service representative, and temperature of the service representative;
    assigning the new assignment to a service representative of the subset, wherein a corresponding anxiety level of the service representative is the least among all service representatives of the subset;
    computing mean and mode anxiety levels corresponding to a service representative of the first queue during a duration the service representative is servicing an assignment, wherein the mean and mode anxiety levels computed are recorded in the historical data; and
    in response to mean anxiety levels corresponding to a service representative of the first queue exceeding a configurable threshold indicating increased physiological stress, marking the service representative as unavailable for assignment, and re-assigning at least one assignment of the second queue.

\* \* \* \* \*